United States Patent [19]
Teach et al.

[11] 4,238,503
[45] Dec. 9, 1980

[54] ANILIDE UREA BIOCIDES

[75] Inventors: Eugene G. Teach, El Cerrito; Don R. Baker, Orinda, both of Calif.

[73] Assignee: Stauffer Chemical Company, Westport, Conn.

[21] Appl. No.: 16,464

[22] Filed: Mar. 1, 1979

Related U.S. Application Data

[60] Division of Ser. No. 792,291, Apr. 29, 1977, Pat. No. 4,159,344, which is a continuation of Ser. No. 605,088, Aug. 15, 1975, abandoned, which is a continuation of Ser. No. 443,539, Feb. 19, 1974, abandoned.

[51] Int. Cl.³ .................... A01N 47/10; A01N 47/28
[52] U.S. Cl. .................... 424/300; 424/322; 260/453 RW; 260/455 A; 564/50; 560/27; 560/30
[58] Field of Search ............ 71/67, 118, 120, 111; 424/322, 300, 324, 320

[56] References Cited
U.S. PATENT DOCUMENTS

| | | | |
|---|---|---|---|
| 2,795,610 | 6/1957 | Gertovich | 71/67 |
| 2,951,010 | 8/1960 | O'Neill et al. | 424/322 |
| 3,184,301 | 5/1965 | Martin et al. | 71/106 |
| 3,652,630 | 3/1972 | Brown | 71/67 |
| 3,860,644 | 1/1975 | Krenzer et al. | 71/67 |
| 3,867,426 | 2/1975 | Olin et al. | 71/120 |
| 3,885,947 | 5/1975 | Baker et al. | 71/67 |
| 3,897,493 | 7/1975 | Teach | 71/111 |
| 4,159,344 | 6/1979 | Teach et al. | 71/118 |

*Primary Examiner*—Glennon H. Hollrah
*Attorney, Agent, or Firm*—Michael J. Bradley

[57] ABSTRACT

This invention relates to the utility of certain anilide ureas as biocidal agents having the formula

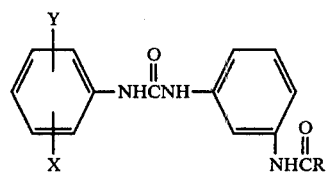

R is selected from the group of alkyls having from 1 to 6 carbon atoms, haloalkyls having from 1 to 6 carbon atoms, $NR_1R_2$, $NHR_1$, $OR_1$ and $SR_1$ in which $R_1$ and $R_2$ are independently lower alkyl having from 1 to 6 carbon atoms, X and Y are independently selected from the group consisting of H, Cl, $CF_3$ and $NHCOR_3$ and $R_3$ is selected from the group of lower alkyl having from 1 to 6 carbon atoms, haloalkyl having from 1 to 6 carbon atoms, $NR_4R_5$, $NHR_4$, $OR_4$ and $SR_4$ in which $R_4$ and $R_5$ are independently lower alkyl having from 1 to 6 carbon atoms.

8 Claims, No Drawings

ANILIDE UREA BIOCIDES

This is a divisional of application Ser. No. 792,291, filed Apr. 29, 1977, now U.S. Pat. No. 4,159,344, which is a continuation of application Ser. No. 605,088, filed Aug. 15, 1975, now abandoned, which is a continuation of application Ser. No. 443,539, filed Feb. 19, 1974, now abandoned.

DETAILED DESCRIPTION OF THE INVENTION

This invention relates to the utility as biocidal agents for the control of bacteria, fungi and algae when used in a biocidally effective amount of certain anilide ureas having the formula

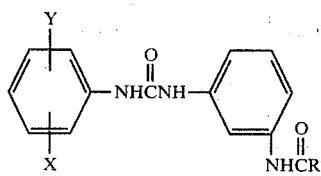

R is selected from the group of alkyl having from 1 to 6 carbon atoms, haloalkyl having from 1 to 6 carbon atoms, $NR_1R_2$, $NHR_1$, $OR_1$ and $SR_1$ in which $R_1$ and $R_2$ are independently lower alkyl having from 1 to 6 carbon atoms, X and Y are independently selected from the group consisting of H, Cl, $CF_3$ and $NHCOR_3$ and $R_3$ is selected from the group of lower alkyl having from 1 to 6 carbon atoms, haloalkyl having from 1 to 6 carbon atoms, $NR_4R_5$, $NHR_4$, $OR_4$ and $SR_4$ in which $R_4$ and $R_5$ are independently lower alkyl having from 1 to 6 carbon atoms. More preferably X and Y are Cl and R is $CF_3$ or $C_2F_5$ and most preferably X and Y are Cl in the 3, 5 position and R is $CF_3$ or $C_2F_5$. It was found that these compounds have biocidal activity and provide beneficial results in controlling the growth of bacteria, fungi and algae.

Controlling the growth of bacteria, fungi and algae by employing the compounds described herein can be accomplished by applying a biocidally effective amount to the environment in which the growth of bacteria, fungi and algae is encouraged, a specific example of such is the human mouth. The compounds may be applied to any environmental area which supports the growth and development of bacteria, fungi and algae. By controlling, it is meant the prevention of the growth of the bateria, fungi and algae to be controlled. Preparation of the compounds is described in U.S. Pat. No. 3,642,891. Reference is hereby made to U.S. Pat. No. 3,642,891, disclosure of which is hereby incorporated by reference. The foregoing patent specified herein above basically discloses preparation techniques of the compounds utilized and the method of the present invention.

The following three examples demonstrate the method used in the preparation of the compounds utilized as starting materials to prepare compounds of the present invention.

EXAMPLE 1 m-Nitro pentafluoropropionanilide

Sixty-nine grams of m-nitro aniline is dissolved in 300 ml of acetone with 51 g. of triethylamine and 92 g. of pentafluoropropionyl chloride is bubbled in. The mixture is filtered to remove triethylamine hydrochloride and the acetone removed under vacuum. The product is washed with water and dried to give 140 g. of solid, m.p. 111°–113° C.

EXAMPLE 2 m-Amino pentafluoropropionanilide

Iron powder, 80 g., is suspended in 125 ml of ethyl alcohol and 100 ml of water and 6 ml of concentrated HCl is added. The mixture is heated to reflux and 140 g. of m-nitro pentafluoropropionanilide is added portionwise to keep the mixture at reflux. When reaction is complete, 6 g. of 50% NaOH is added and the mixture filtered to remove iron oxides and the filtrate stripped under vacuum. The product crystallizes from the aqueous solution giving 107 g., m.p. 86°–88° C.

m-Amino trifluoroacetanilide was prepared similarly.

EXAMPLE 3 m-Pentafluoropropionamido phenyl isocyanate

Sixty-three and one half grams of m-amino pentafluoropropionanilide is dissolved in 150 ml of tetrahydrofuran containing 65 g. of triethylamine. This mixture is added dropwise with coolng to 37 g. of phosgene dissolved in 150 ml of tetrahydrofuran cooled to −5° C. When addition is complete the mixture is allowed to warm up to room temperature. The triethylamine hydrochloride is filtered off and the solvent is removed under vacuum. The product, 70 g., was not isolated but diluted to 140 ml with tetrahydrofuran and used in subsequent reactions.

The following three examples illustrate methods of preparation of compounds of the present invention.

EXAMPLE 4

1(m-pentafluoropropionamido phenyl)3(3′,5′-dichlorophenyl) urea

Five and eight-tenths grams of m-propionamido phenyl isocyanate in tetrahydrofuran solution was added to 50 ml of acetone and 3.2 g. of 3, 5-dichloroaniline was added. The mixture was heated to reflux, cooled and stripped of solvents. Yield was 6.5 g. of product m.p. 149–151° C. after trituration with petroleum ether.

EXAMPLE 5

1(m-trifluoroacetamidophenyl)-3(3′,4′-dichlorophenyl) urea

Four and one-tenth grams of m-amino trifluoro acetanilide is dissolved in 100 ml of acetone and 3.8 g. of 3,4-dichlorophenyl isocyanate is added. The mixture is heated to reflux and crystallizes from acetone on cooling. Yield is 6.4 g., m.p. 221°–223° C.

EXAMPLE 6

1(m-pentafluoropropionamido phenyl)3(3′,4′-dichlorophenyl) urea

Five and one-tenth grams of m-amino pentafluoropropionanilide is dissolved in 50 ml of acetone and 3.8 g. of 3,4-dichlorophenyl isocyanate is added. The mixture is heated to reflux, cooled and the acetone stripped off under vacuum. Yield is 8.8 g., m.p. 195°–197° C.

Other compounds of this invention were prepared in a similar manner.

The compounds utilized in this invention and exemplified in the following biocidally active compounds as examples are as follows:
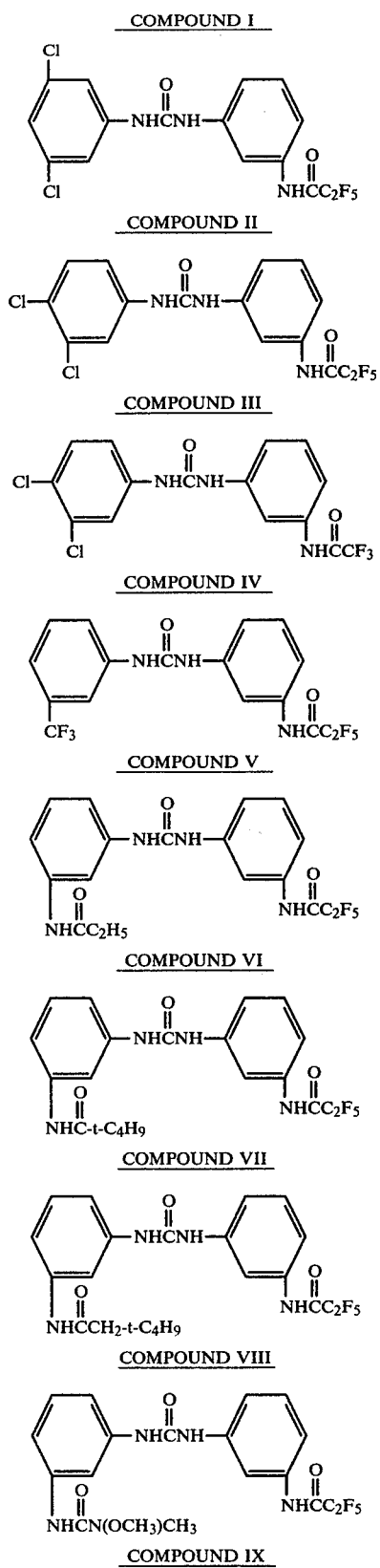
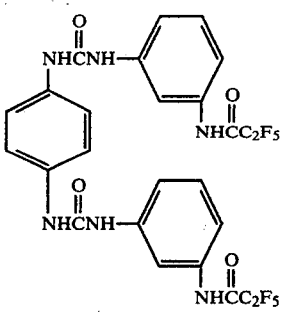
COMPOUND X
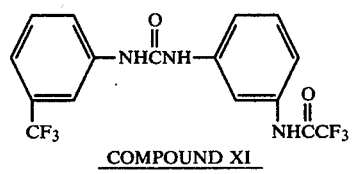
COMPOUND XI
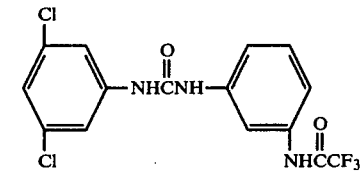
COMPOUND XII
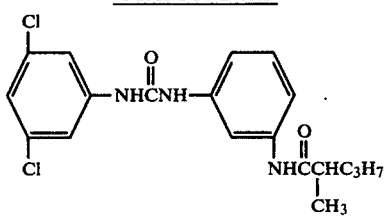
COMPOUND XIII
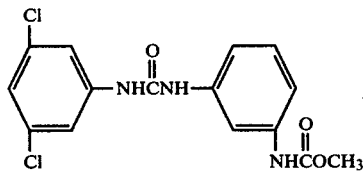
COMPOUND XIV
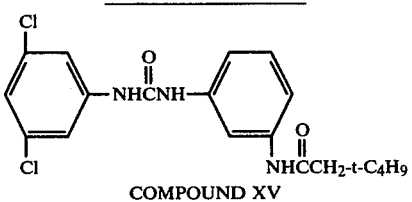
COMPOUND XV
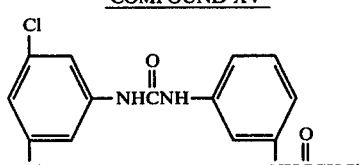
COMPOUND XVI
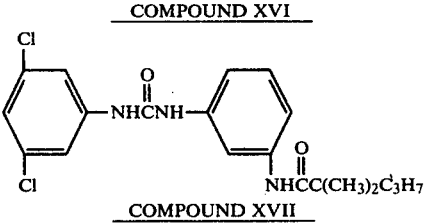
COMPOUND XVII -continued

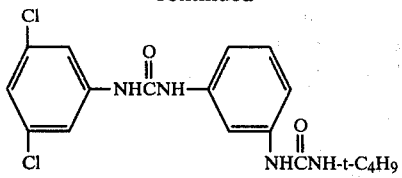

These compounds will be hereinafter referred to as Compound I, Compound II and Compound III, etc., in the following examples.

EXAMPLE 7

Biocide Testing Procedure

Tubes of sterilized nutrient and malt extract broth are prepared. Aliquots of the toxicant, dissolved in an appropriate solvent, are injected through the stopper, into the broth, to provide concentrations ranging from 50 ppm downward. The test organism is a fungi, *Phoma herbarum*. Three drops of a spore suspension of the fungi are injected into the tubes of malt broth. One week later the growth of the organism is observed and effectiveness of the chemical is recorded as the lowest concentration in ppm which provides 50% inhibition of growth as compared to untreated tube. The results of these tests are tabulated in Table I.

TABLE I

|  | μgm/ml |
|---|---|
| Compound 1 | >50 |
| Compound 2 | >50 |
| Compound 3 | (50) |

>greater than
()indicates partial control of this concentration

EXAMPLE 8

In Vitro Agar Screening Tests

This test measures the bactericidal, fungicidal and algaecidal properties of a compound when in contact with growing bacteria, fungi or algae in an artificial medium. The test is conducted by adding 20 ml. portions of a suitable warm sterile agar solution into 20×100 mm. Petri dishes. Then, the test compound, in 0.5% acetone solution, is added to the Petri dishes at levels of 1, 5, 10 and 50 μg/ml. and mixed with the warm mobile agar solution. The treated agar mixture is then allowed to come to room temperature and solidify. Cells of the chosen organism are streaked on the surface of the solidified agar and are then incubated for such lengths of time that untreated samples containing no toxicant show luxurious growth typical of the particular organism. This time varies from 24 hours to one week depending on the particular organism. The fungi are incubated at 30° C. and the bacteria are incubated at 37° C. The algae are incubated at room temperature under artificial light. Nutrient agar is used as the medium in this test for the bacteria. Potato dextrose agar is used as the medium for the fungi with the exception of *Trichophyton mentagrophytes* for which Emmons agar is used. A modified Jack Meyers agar is used for the growth of the algae.

The extent of growth is noted at the end of the incubation period.

Representative organisms used in this test are as follows:
Bacteria
*Enterobacter aerogenes*
*Bacillus cereus*
*Brevibacterium ammoniagenes*
Fungi
*Trichophyton mentagrophytes*
Algae
*Scenedesmus obliquus*

TABLE II

In Vitro Agar Screening Tests
Minimum Inhibitory Concentration, μg/ml.

|  | Compound Number | | |
|---|---|---|---|
|  | I | II | III |
| Bacteria |  |  |  |
| *Enterobacter aerogenes* | 5 | 5 | 5 |
| *Bacillus cereus* | (1) | (1) | 5 |
| *Brevibacterium ammoniagenes* | (1) | (5) | (10) |
| Fungi |  |  |  |
| *Trichophyton mentagrophytes* | >50 | (50) | >50 |
| Algae |  |  |  |
| *Scenedesmus obliquus* | 5 | (1) | 1 |

()indicates partial control at this concentration
greater than

EXAMPLE 9

Sulfate Reducing Bacteria in Vitro Test

This test measures the bactericidal properties of a compound when in contact with a sulfate reducing bacteria, specifically *Desulfovibrio desulfuricans*. The test is conducted by dissolving the test compound in acetone to give an 0.5% solution. This toxicant is added to vials containing sterile Sulfate API broth with tryptone under anaerobic conditions at such levels to give final toxicant concentrations of 1, 5, 10 and 50 μg/ml. of solution. An inoculant solution of 0.5 ml. of the growing organism, *Desulfovibrio desulfuricans*, is added to the vials followed by sufficient sterile distilled water to give a total of 10 ml. of solution in the vials. The vials are incubated at room temperature for 3 to 5 days until untreated controls show growth of the organism as indicated by the black color development in the vials.

The following es a summary of the minimum inhibitory concentration necessary to control the organism.

TABLE III

|  | μg/ml | | |
|---|---|---|---|
|  | Compound I | Compound II | Compound III |
| *Desulfovibrio desulfuricans* | (10) | (50) | (50) |

()indicates partial control at this concentration.

EXAMPLE 10

*Staphylococcus aureus* Use Dilution Test

This test measures the bacteriostatic effectivenss of a particular test compound against *Staphylococcus aureus*.

Tryptic Soy Broth is dispensed aseptically into sterile 13×100 mm. clear glass culture tubes. The first tube receives 3.6 ml. of medium and tubes 2 through 10 receive 2.0 ml. of medium. The test compound is dissolved in acetone to give 10 ml. of a solution of 0.10% of the test compound. Using a sterile syringe, 0.4 ml. of the test compound solution is placed in the first tube containing the 3.6 ml. of sterile broth and mixed thoroughly. This operation is continued through to the tenth tube. From the tenth tube, 2.0 ml. of solution is removed and discarded. Each tube is then innoculated with 0.1 ml. of a 24 hour culture of *Staphylococcus aureus* in Tryptic Soy Broth, and the mixture is mixed thoroughly using a Vortex mixer. A control is also set up to be sure that the inoculum is viable using a tube of sterile broth containing no added toxicant. The tubes are incubated for 24 hours at 37° C. The tubes are then examined to determine growth of the organism in the culture tubes. The minimum concentration in which no growth of the organism occurs is recorded. The following table gives the minimum inhibitory concentration necessary to control the organism:

TABLE IV

| Toxicant | Minimum Inhibitory Concentration<br>*Staphyloccus aureus*, μg/ml. |
|---|---|
| Compound I | 1.56 |
| Compound II | 3.12 |
| Compound III | 25.00 |

*Staphhylococcus aureus* In Vitro Bio Assembly Test

BIOCIDE TESTING PROCEDURES

Tubes of sterilized nutrient and malt extract broth are prepared. Aliquots of the toxicant, dissolved in an appropriate solvent, are injected through the stopper, into the broth, to provide concentrations ranging from 50 ppm downward. The test organism consists of a bacteria, *Staphylococcus aureus* Rosenbach. Three drops of the bacteria suspension are injected into the nutrient broth. One week later the growth of the bacteria is observed and effectiveness of the chemical is recorded as the lowest concentration in ppm which provides 50% inhibition of growth as compared to untreated inoculated tubes.

TABLE V

| Toxicant | Minimum Inhibitory Concentration<br>PPM |
|---|---|
| Compound I | 0.06 |
| Compound II | 0.06 |
| Compound III | 0.25 |
| Compound IV | 0.13 |
| Compound V | 0.5 |
| Compound VI | 5 |
| Compound VII | 10 |
| Compound VIII | 10 |
| Compound IX | 10 |
| Compound X | 5 |
| Compound XI | 0.25 |
| Compound XII | 1.0 |
| Compound XIII | 50 |
| Compound XIV | 1.0 |
| Compound XV | 0.5 |
| Compound XVI | 0.25 |
| Compound XVII | 5 |

The compounds of this invention are generally embodied into a form suitable for convenient application. For example, the compounds can be embodied into pesticidal compositions which are provided in the form of emulsions, suspensions, solution, dusts and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions of this inventon can contain, as adjuvants, organic solvents such as sesame oil, xylene range solvents, heavy petroleum, etc; water, emulsifying agents; surface active agents; talc; pyrophyllite; diatomite; gypsum; clays; propellants, such as dichlorodifluoromethane, etc. If desired, however, the active compounds can be applied directly to feedstuffs, seeds, etc. upon which pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition; for example, an emulsion, suspension, or aerosol spray. While the concentration of the active pesticide in the present pesticidal compositions can vary within the rather wide limits, ordinarily the pesticide compound will comprise not more than about 15.0% by weight of the pesticidal composition. Preferably, however, the pesticide compositions of this invention will be in the form of solutions or suspensions containing about 0.1 to 1.0% by weight of the active pesticide compound.

What is claimed is:

1. The method of controlling bacteria and fungi comprising applying to the habitat thereof, an effective amount of a compound having the formula

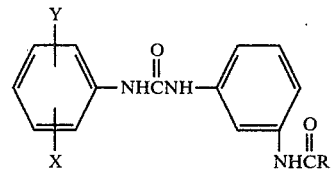

R is selected from the group of alkyl having from 1 to 6 carbon atoms and haloalkyl having from 1 to 6 carbon atoms, $NHR_1$, $OR_1$ in which $R_1$ is lower alkyl having from 1 to 6 carbon atoms, X and Y are independently selected from the group consisting of H, $NHCOR_3$ and $R_3$ is selected from the group of lower alkyl having from 1 to 6 carbon atoms provided that when X is hydrogen Y is $NHCOR_3$.

2. A method of controlling bacteria and fungi as set forth in claim 1 wherein the compound is

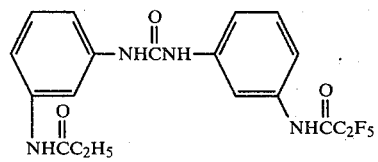

3. A method of controlling bacteria and fungi as set forth in claim 1 wherein the compound is

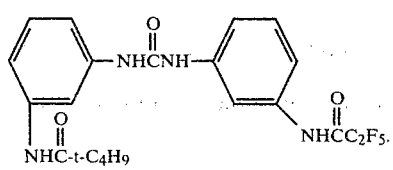

4. A method of controlling bacteria and fungi as set forth in claim 1 wherein the compound is

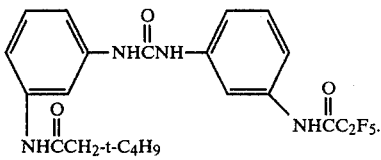

5. A method of controlling bacteria and fungi comprising applying to the habitat thereof, an effective amount of a compound having the formula

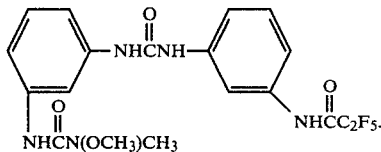

6. A method of controlling bacteria and fungi comprising applying to the habitat thereof, an effective amount of a compound having the formula

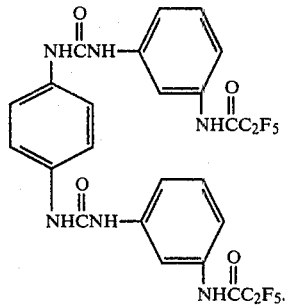

7. A method of controlling bacteria and fungi comprising applying to the habitat thereof, an effective amount of a compound having the formula

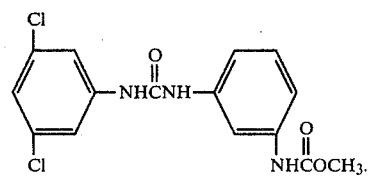

8. A method of controlling bacteria and fungi comprising applying to the habitat thereof, an effective amount of a compound having the formula

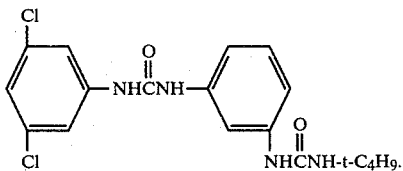

* * * * *